United States Patent [19]

Banjanin

[11] Patent Number: 5,544,659
[45] Date of Patent: Aug. 13, 1996

[54] ULTRASONIC DOPPLER IMAGER HAVING A REDUCED HARDWARE ADAPTIVE TISSUE REJECTION FILTER ARRANGEMENT

[75] Inventor: Zoran B. Banjanin, Renton, Wash.

[73] Assignee: Siemens Medical Systems, Inc., Iselin, N.J.

[21] Appl. No.: 366,206

[22] Filed: Dec. 29, 1994

[51] Int. Cl.$^6$ ...................................................... A61B 8/00
[52] U.S. Cl. ........................................................ 128/661.09
[58] Field of Search ............................ 128/661.07–661.1, 128/602.01; 73/861.25

[56] References Cited

U.S. PATENT DOCUMENTS

| | | | |
|---|---|---|---|
| 4,583,552 | 4/1986 | Iimura et al. | 73/861.25 X |
| 4,830,016 | 5/1989 | Tamano et al. | 128/661.09 |
| 4,896,674 | 1/1990 | Seo | 128/661.09 |
| 4,961,427 | 10/1990 | Namehawa et al. | 128/661.09 |
| 5,107,841 | 4/1992 | Sturgill | 128/661.09 |
| 5,170,792 | 12/1992 | Sturgill et al. | 128/661.09 |
| 5,197,477 | 3/1993 | Peterson et al. | 128/661.08 |
| 5,228,009 | 7/1993 | Foriestori et al. | 367/135 |
| 5,383,464 | 1/1995 | Shiba | 128/661.09 |
| 5,445,156 | 8/1995 | Daft et al. | 128/661.08 |

OTHER PUBLICATIONS

"Introduction to Roda Systems", Skolnik, M. T., McGraw-Hill ©1962 N.Y., N.Y. pp. 148–170.

*Primary Examiner*—Francis Jaworski
*Attorney, Agent, or Firm*—Lawrence C. Edelman

[57] ABSTRACT

An ultrasonic Doppler flow (e.g. blood) imaging and/or measuring system capable of adaptively suppressing stationary or slowly-moving non-flow (e.g. tissue) signals having variable spectra from the recovered ultrasonic echoes. In accordance with the invention, the tissue signals are suppressed using a tissue rejection filter arrangement having an attenuation characteristic which is controlled based upon measured estimates of at least one spectral characteristic of the tissue signals to be removed, thereby maximizing the rejection of tissue movement signals and minimizing undesired attenuation of the blood flow signals. In accordance with an embodiment of the invention, signal routing out of the corner-turning buffer memory component in prior art systems is advantageously modified, so as to provide during a first mode of operation, the echo signal data to a Doppler velocity processor, for forming estimates of tissue signal motion. These estimates are then used for developing a control signal for application to a tissue motion rejection filter arrangement. During a second mode of operation, the echo signal data are provided to the same Doppler velocity processor, however, this time via the tissue motion rejection filter arrangement. Thus, the estimates of tissue signal motion are developed in a simplified hardware arrangement, by using the same corner turning memory and Doppler velocity processing circuitry as is used for developing the blood flow velocity signals.

17 Claims, 7 Drawing Sheets

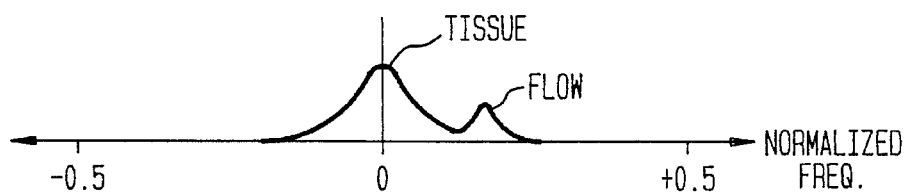
FIG. 5A
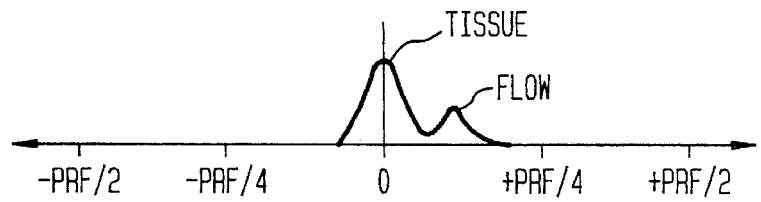
FIG. 5B
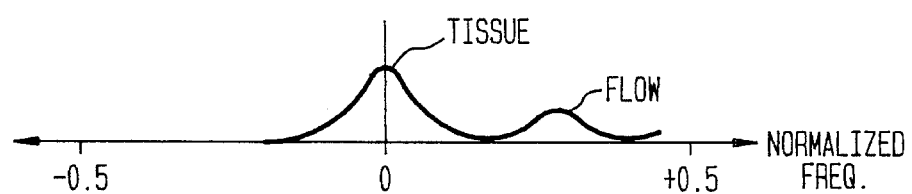
FIG. 5C
FIG. 6A
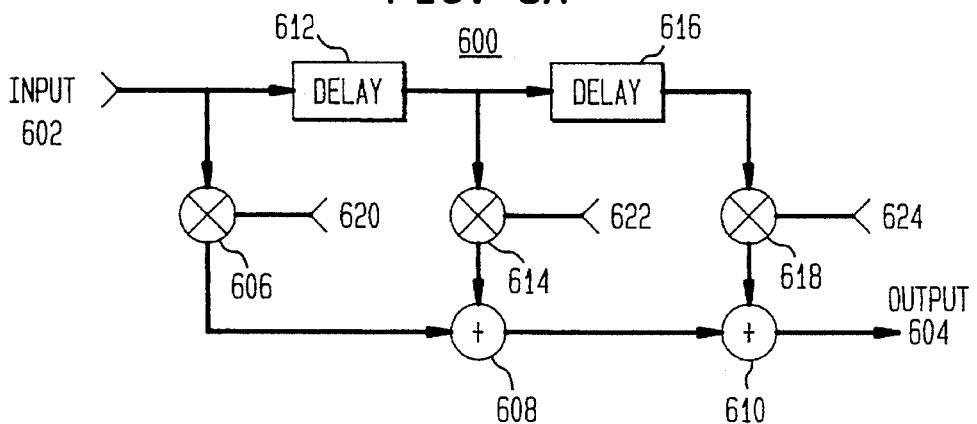
FIG. 6B
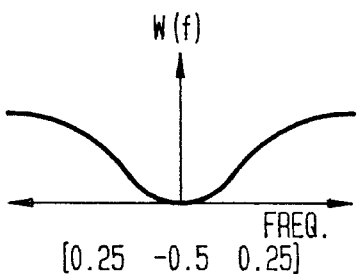
FIG. 6C
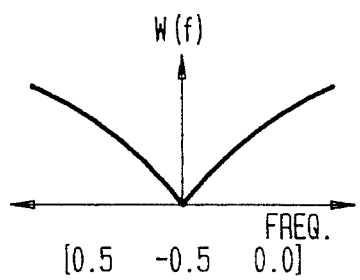

ULTRASONIC DOPPLER IMAGER HAVING A REDUCED HARDWARE ADAPTIVE TISSUE REJECTION FILTER ARRANGEMENT

CROSS REFERENCE TO RELATED APPLICATIONS

This application is related to the following four U.S. patent applications, which: (a) are being filed concurrently herewith; (b) are assigned to the same assignee; (c) deal with related subject matter; and (d) share inventors in common. The related patent applications are entitled:

1. Ultrasonic Doppler Imager Having A Spatially Smoothed Control Signal For An Adaptive Tissue Rejection Filter filed on Dec. 29, 1994 as U.S. Ser. No. 08/365,660;
2. Ultrasonic Doppler Imager Having An Adaptive Tissue Rejection Filter With Enhanced Tissue Motion Sensitivity, filed on Dec. 29, 1994 as U.S. Ser. No. 08/366,067;
3. Ultrasonic Doppler Imager Having An Adaptive Tissue Rejection Filter, filed on Dec. 29, 1994 as U.S. Ser. No. 08/365,668; and
4. Ultrasonic Doppler Imager Having An Adaptive Tissue Rejection Filter With Variable Parameters, filed on Dec. 29, 1994 as U.S. Ser. No. 08/366,163.

BACKGROUND OF THE INVENTION

1. Field of the Invention

This invention relates to an ultrasonic Doppler flow imaging and/or measuring system.

2. Description of the Background Art

This invention pertains to ultrasound imaging techniques, and finds particular use in medical diagnostic applications. It is known that a medical ultrasound imaging system can be used to display and analyze anatomical structures within a patient's body. The ultrasound imaging system transmits sound waves of very high frequency, typically 2 to 10 MHz, into the patient's body and processes echoes reflected from tissues and materials within the patient's body. A number of different types of displays are provided by ultrasound imaging systems but probably the most popular display is a two-dimensional (2D) image of selected cross-sections of the body. In an echo mode of operation, all echoes from a selected cross-section are processed and displayed. Use of the echo mode of operation enables a sonographer to detect a number of anatomical defects. Further, the size of such defects can be more or less precisely determined. The performance of the echo mode of operation is determined by the size of a resolution cell and, as is well known, the size of a resolution cell can be decreased by utilizing dynamic focusing and dynamic (matched) filtering.

In some clinical applications, anatomical defects can be relatively small, and echoes produced by such small anatomical defects are overshadowed by larger echoes from surrounding tissue. However, such small anatomical defects may be seen by displaying changes in blood flow velocity. As is well known, Doppler measurements can be used to determine the velocity of a moving object and a display of Doppler shifts caused by blood flow enables small anatomical defects to be detected more easily. This mode of operation wherein Doppler shifts caused by blood flow are displayed is known in the art as Color Flow. For example, U.S. Pat. No. 4,800,891 issued to Kim, and assigned to the same assignee as the present invention, describes the color flow process and how Doppler information relating to blood flow velocity can be gathered from large selected cross-sections of an anatomical structure under study. A color flow processor is used to develop estimates of three spectral moments of a flow signal, e.g., its power, velocity, and variance. These estimates are then used to cause the ultrasound system to display a 2D color flow image during a color flow mode of operation.

It is difficult to acquire sufficient ultrasound data to develop an accurate, high resolution, blood flow image at a high rate. Thus, in order to obtain more precise Doppler information about blood flow velocity from a small cross-sectional area, as is well known, the spectral Doppler mode of operation is used, such as described, for example, in the article entitled "Extraction of Blood Flow Information Using Doppler-Shifted Ultrasound", by Halberg and Thiele, published in the Hewlett-Packard Journal, pp. 35–40, June 1986. In the spectral Doppler mode of operation it is possible to devote more time to a selected small area. The results of the spectral Doppler mode of operation are conventionally displayed by means of a frequency spectrum and an audio signal.

One of the more problematic areas in diagnostic Doppler processing is effective removal of unwanted signals from tissue reflections which, due to their large amplitude, can overshadow and thereby mask the desired blood flow signals. Removal of signals arising from tissue movement is conventionally accomplished with a high pass filter (HPF). The design of this filter incorporates certain assumptions about the maximum frequency of tissue (or clutter) signals and the necessary corresponding cut-off frequency of this HPF. The filter is then designed according to this cut-off frequency. However, in practice, the spectrum of clutter signals is not stationary, due to cardio-pulmonary motion in the human body and also the intentional and non-intentional movement of the ultrasound probe by the operator of the diagnostic equipment.

Similar problems arise in radar applications of similar techniques (i.e. processing techniques for echoes of electromagnetic signals), and many different techniques for the removal of unwanted signals (generally referred to as "clutter") have been used. The reference entitled "Radar Handbook", by M. I. Skolnik (McGraw-Hill Book Co., New York, 2nd Ed. 1990) describes several of these techniques. One such technique described in this reference is known as the TACAR system for airborne radar systems.

A method similar to the TACAR system, and adapted for application to ultrasound systems, is described in U.S. Pat. No. 4,961,427, issued to Namekawa. In this approach, as well as in the TACAR system, compensation for clutter movement is carried out on the received signal during its downconversion to baseband, using an RF signal mixer.

In another approach, described in U.S. Pat. No. 5,170,792, issued to Sturgill et al., compensation for clutter movement is performed on the received signal after its frequency downconversion to baseband signal components. Since the baseband signal is a complex signal-(i.e., having In-phase (I) and Quadrature (Q) components), tissue movement (clutter) compensation is carried out during a complex mixing operation using a tissue velocity signal as the complex reference signal. In each of these previously mentioned approaches, as well as all other approaches known to the inventors herein, although special circuits may be used for estimation of tissue (clutter) velocities, only the change of mean tissue frequency is compensated for by the reference signal. However, in an ultrasound system, tissue movements are also accompanied by changes in other spectral moments of the tissue signal, e.g., its power and spectral width. Changes of these parameters are not considered by the foregoing techniques, and therefore the effectiveness of prior art tissue/clutter rejections based only on compensation of tissue mean velocity is relatively limited, especially in diagnostic ultrasound applications.

SUMMARY OF THE INVENTION

The present invention provides an ultrasonic Doppler blood (i.e. flow) imaging and/or measuring system capable of adaptively suppressing stationary or slowly-moving tissue (i.e. non-flow) signals having variable spectra, from the recovered ultrasonic echoes. In accordance with the invention, the tissue signals are suppressed using a tissue rejection filter having an attenuation characteristic which is controlled based upon a measured estimate of at least one spectral characteristic of the tissue signals to be removed, thereby maximizing the rejection of tissue movement signals and minimizing undesired attenuation of the blood flow signals.

In accordance with an embodiment of the invention, advantage is taken of the fact that signal routing out of the "corner-turning" buffer memory (a conventional component in prior art systems) can be modified so as to provide during a first mode of operation, the echo signal data to a Doppler velocity processor for forming estimates of tissue signal motion. These estimates are then used for developing a control signal for application to a tissue motion rejection filter arrangement. During a second mode of operation, the echo signal data are provided to the same Doppler velocity processor, however, this time via the tissue motion rejection filter. Thus, the estimates of tissue signal motion are developed in a simplified hardware arrangement, by using the same Doppler velocity processing circuitry as is used for developing the blood flow velocity signals.

BRIEF DESCRIPTION OF THE DRAWINGS

FIG. 3b shows a detail of one of the color flow beamlines illustrated in FIG. 3a;

FIG. 5 illustrates the effect of periodically skipping the read-out of data from a corner turning memory portion of the color flow processor shown in FIG. 4;

FIG. 6a shows an embodiment of a digitally programmable filter useful for constructing a tissue rejection filter of the type shown in FIG. 4, and FIG. 6b and FIG. 6c show examples of selectable frequency responses for the filter of FIG. 4;

FIG. 7 shows a complex notch filter embodiment for the tissue rejection filter shown in FIG. 4, using four of programmable filters of the type shown in FIG. 6a;

In the above FIGURES, common reference numbers are used throughout to indicate the use of common elements.

DETAILED DESCRIPTION OF THE PREFERRED EMBODIMENTS

Figure 1:
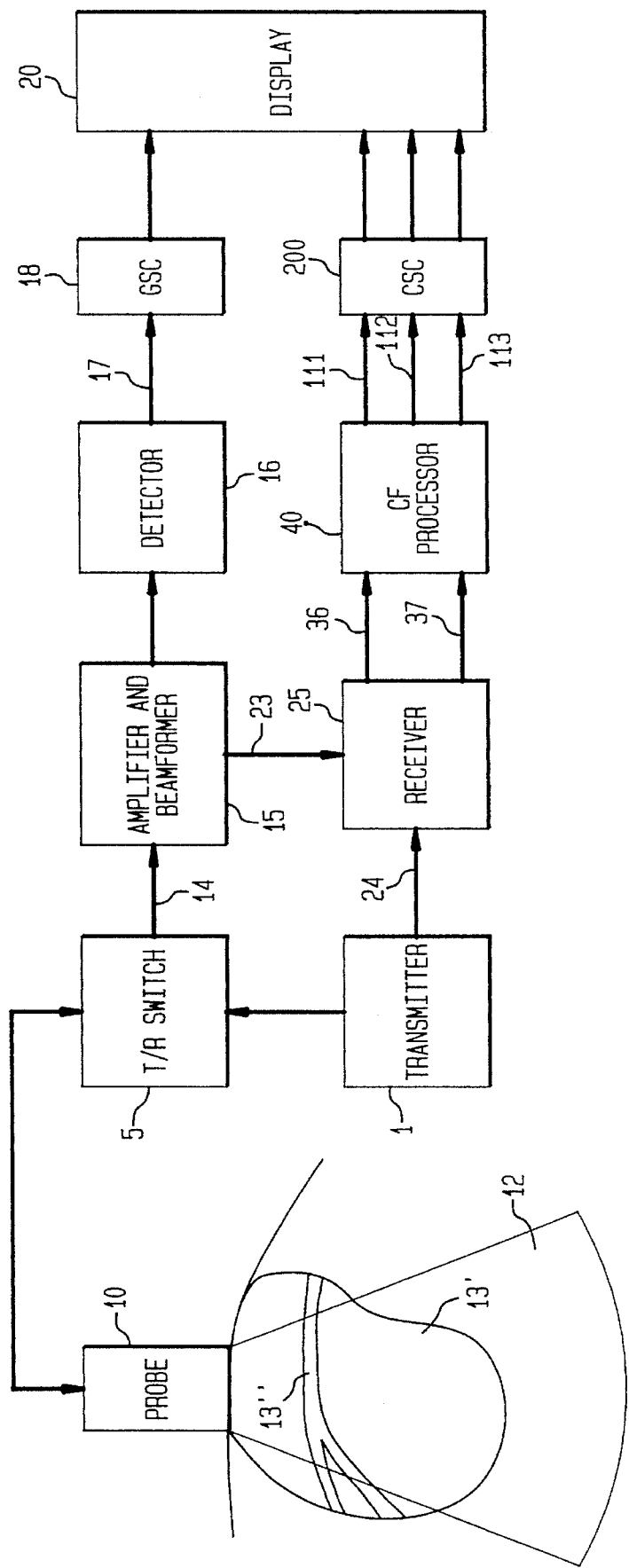
FIG. 1 shows a block diagram of an ultrasound imaging system which is fabricated in accordance with one embodiment of the present invention for providing diagnostic blood flow imaging using Doppler techniques.

FIG. 1 shows a block diagram of one embodiment of an ultrasound imaging apparatus in which the present invention is useful, which apparatus includes a color flow processor for providing a Doppler blood flow imaging mode of operation. Transmitter 1 generates an electronic signal at high frequency, typically 2–10 MHz. The electronic signal is amplified and sent to ultrasound transducer probe 10 through transmitter-receiver (T/R) switch 5. T/R switch 5 provides isolation of sensitive amplifying circuitry in amplifier and beamformer 15 during a transmit phase. Probe 10 converts the electronic signal received from transmitter 1 into an ultrasonic pulsed wave and launches the pulsed wave into scanned body 12 of a patient, which scanned body 12 is shown pictorially in FIG. 1.

As shown in FIG. 1, a scanned area 12 in a body of a patient is comprised of relatively stationary anatomical tissue 13, including , e.g., organs 13' and blood vessels 13". Echoes of the ultrasonic pulsed wave are received by probe 10 from scanned area 12. The echoes result from reflections of the launched electronic pulse wave from objects in scanned area 12, and are generally comprised of relatively large amplitude echoes from tissue 13 , and relatively small amplitude echoes from blood which is flowing in blood vessels 13". Probe 10 includes a plurality of individual transducer elements which convert these ultrasonic echoes into electrical echo signals. The electrical echo signals are then sent, via T/R switch 5, to amplifier and beamformer 15. In amplifier and beamformer 15, separate echo signals from each transducer element of probe 10 are amplified and digitized, appropriately delayed relative to one another, and then combined to produce a plurality of beamline signals which are applied as input to gray scale detector 16 and receiver 25. Gray scale detector 16 extracts a low frequency envelope signal from its input signal and transmits the low frequency envelope signal over signal channel 17 to gray scale scan converter (GSC) 18. Gray scale scan converter 18 rearranges the scan order of the low frequency envelope signal and applies it as input to display sub-system 20 where it is displayed as a gray scale image in a manner which is well known to those of ordinary skill in this art.

As known, an echo signal received from tissue 13 is usually much stronger than an echo signal received from blood flow in blood vessels 13". As a result, in a gray scale image the blood flow image is substantially obscured by features of tissue image. In order to overcome this effect when trying to generate a color flow image of blood flow, additional processing is performed in receiver 25 and color flow processor 40. In particular, receiver 25 converts the relatively high frequency RF beamline signals received from amplifier and beamformer 15 over channel 23 to relatively low frequency quadrature (I and Q) baseband beamline signals and transmits these baseband signals over channels 36 and 37 to color flow processor 40. Receiver 25 converts the RF beamline signals using as a reference an RF signal which it receives over channel 24 from transmitter 1 which was used to generate the launched ultrasonic pulse waves. In response to the quadrature baseband signals input from receiver 25, color flow processor 40 develops estimates of various parameters of the beamline signals which are representative of movement in the scanned area and transmits these estimates over channels 111, 112, and 113 to color flow scan converter (CSC) 200. Color flow scan converter 200 converts the scanning order of these estimated parameters to a format suitable for forming a color blood flow image and sends these estimates to display sub-system 20. In response, display sub-system 20 overlays the above-described gray scale image with a color blood flow image in a manner which is well known to those of ordinary skill in this art.

As also well known by those of ordinary skill in this art, ultrasound imaging systems can have an analog beamformer, a digital beamformer or a hybrid beamformer which is part digital and part analog. In those having an analog beamformer, conversion of signals from analog to digital form is usually performed by analog to digital (A/D) conversion of signals output by gray scale detector 16 and of signals output by receiver 25. In systems having a digital beamformer, A/D conversion is performed prior to digital beamforming. The embodiments shown herein are generally described in the environment of digital beamforming, but it should be understood that all embodiments of the invention as will be described herein could use analog beamforming as well.

Figure 2:
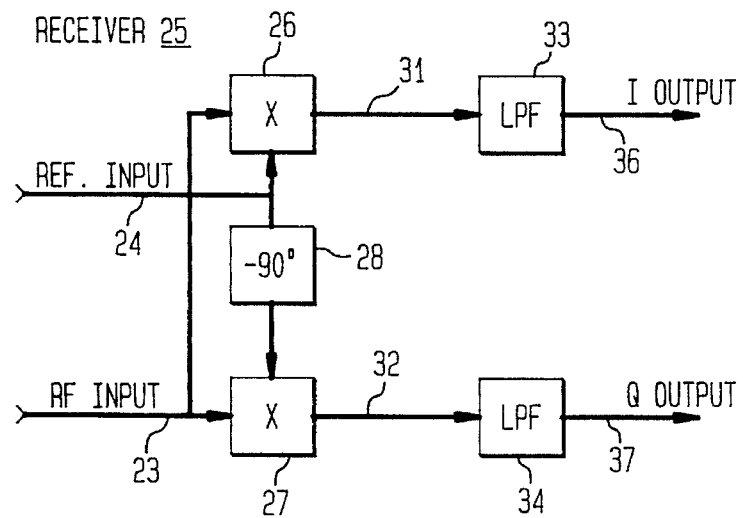
FIG. 2 shows a block diagram of a signal receiver portion of the imaging system shown in FIG. 1.

FIG. 2 shows a block diagram of receiver 25. As shown in FIG. 2, an RF beamline input signal is received from amplifier and beamformer 15 over channel 23. This RF input signal is applied as input to mixers 26 and 27. As further shown in FIG. 2, the RF reference signal received over channel 24 from the transmitter 1 is applied as input to mixer 26 and to phase shifter 28. Phase shifter 28 phase shifts the reference signal by −90 degrees and applies the shifted output as input to mixer 27. As is conventional, mixers 26 and 27 are signal multipliers, and are used to downconvert the RF input signal into baseband (lower frequency) In-phase (I) and Quadrature (Q) signals, respectively. The I and Q signals from mixers 26 and 27 are applied as input over channels 31 and 32, respectively, for selecting the baseband I and Q components by filtering in low-pass filters, 33 and 34, respectively. The resulting filtered signals output from low pass filters 33 and 34 are transmitted to color flow processor 40 over channels 36 and 37. As noted above, in the preferred embodiment, receiver 25 is constructed using digital techniques.

Figure 3A:
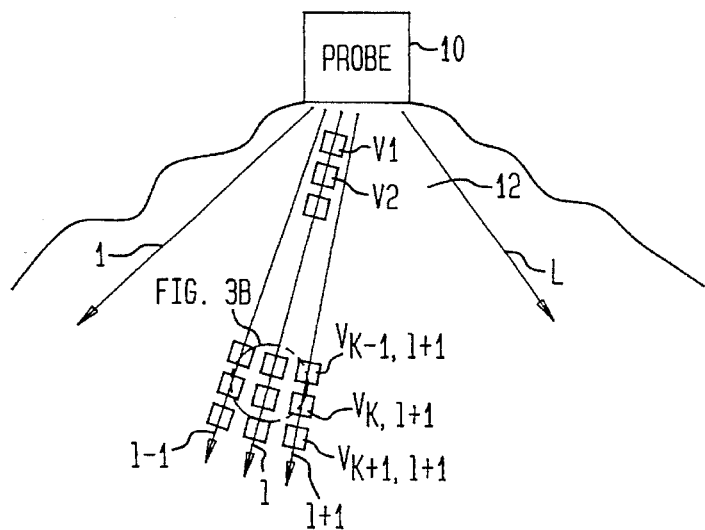
FIG. 3a shows, in pictorial form, a region of a body being scanned by a set of color flow beamlines generated by the ultrasound imaging system of FIG. 1.
Figure 3B:
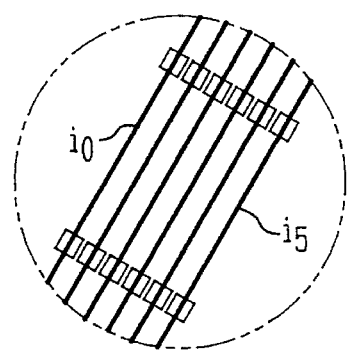

As is known, during color flow imaging, multiple vectors or acoustic lines (commonly referred to as a vector or acoustic line "ensemble") are processed for each beamline direction in a color flow scan area, in order to enable estimation of parameters of the color flow signal, see for example, the above-referenced patent of Kim. FIG. 3a shows, in pictorial form, an area of a body being scanned by an ultrasound imaging system and indicates resolution volumes for several ultrasound beamlines. Scanning probe 10 gathers data from a plurality of different beamlines, which beamlines are denoted by an index l=1, 2 . . . L, wherein L may typically be 64, 128 or 256. Data gathered axially along a given beamline l are divided into a sequence of resolution volumes $V_1, V_2, \ldots V_K$, for K range gates, wherein K may typically range from 32 to 1024 or more. FIG. 3b shows a detail of one beamline l and illustrates an ensemble of six acoustic lines $i_0$–$i_5$ developed by six firings of probe 10 for each beamline direction. Note, in FIG. 3b, the acoustic lines are illustrated as being side-by-side to show the repetitive firings of probe 10, and are not illustrative of a spatial shift between the firings.

Figure 4:
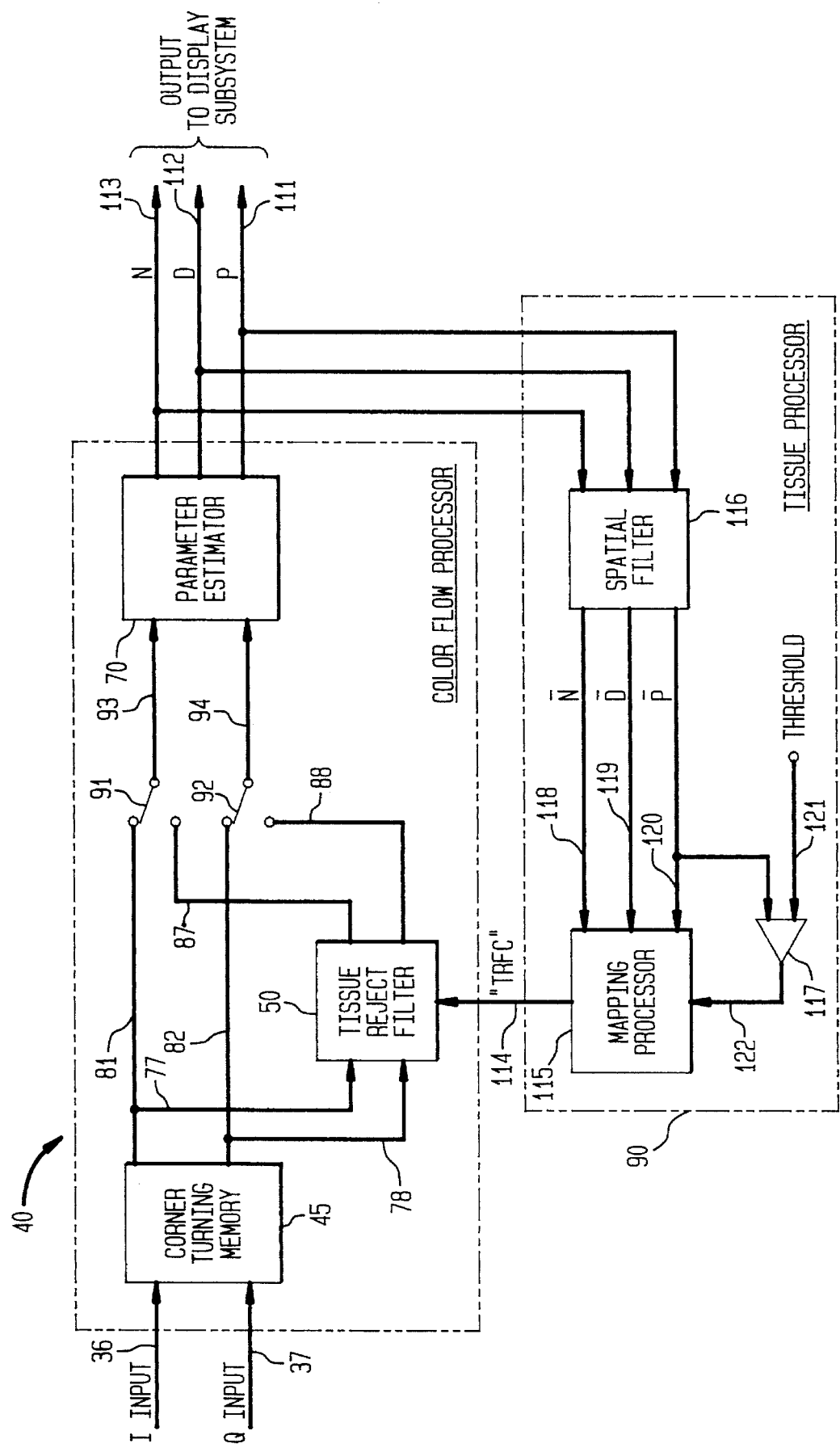
FIG. 4 shows a block diagram of a color flow processor which is fabricated in accordance with an embodiment of the present invention for implementing adaptive rejection of tissue signals during the Doppler mode of operation of the imaging system shown in FIG. 1.

FIG. 4 shows a block diagram of color flow processor 40 which is fabricated in accordance with an embodiment of the present invention for implementing adaptive rejection of tissue signals during the Doppler mode of operation. Note, as used herein, the word "tissue" corresponds to the "non-flow" portions of the scanned area, such as the blood vessel walls which may be slowly moving due to their expansion/contraction in response to pulsatile blood flow, or the apparent movement of stationary body portions due to operator movement of the ultrasonic probe. As shown in FIG. 4, the baseband I and Q signal samples received from receiver 25 over channels 36 and 37 are stored in corner turning memory 45. As is conventional in the art, acoustic line signal samples are written into (input into) corner turning memory 45 in the time order that they are received during the ultrasound scanning, but are read from (output from) corner turning memory 45 in a different sequence, i.e., from an acoustic line which is adjacent in time, and at the same depth (i.e., at the same range gate). The process of providing signal samples in this manner is called corner turning (hence the name corner turning memory) and is similar to matrix transposition. This can be understood by visualizing the data as being organized as a matrix wherein time sequential acoustic lines correspond to adjacent columns in the memory and sequential scanning depths correspond to adjacent rows in the memory. Using this picture, during operation of corner turning memory 45, the matrix from which data is read (output) is the transpose of the matrix into which the data was written (input).

In color flow processor 40 shown in the FIG. 4 embodiment of the invention, data stored in corner turning memory 45 are read (output) twice. In the first read operation, data read from corner turning memory 45 are used for tissue motion parameter estimation and, in the second read operation, data read from corner turning memory 45 will be corrected to reject its tissue motion components and produce signals substantially representative of only blood flow. The general operation of this embodiment of the invention can be viewed as follows. During the first read operation, information is developed which controls subsequent filtering of stationary or slowly moving tissue signals (slowly moving as compared, in general, to the movement of blood, i.e., blood flow) from the composite signal, which subsequent filtering occurs during the second read operation. Since the same corner turning memory and, as will be described below, parameter estimator, are used for both read operations, this embodiment of the invention results in a significant reduction in hardware requirements for the apparatus.

Now let us discuss the first read operation. During the first read operation, data read out of corner turning memory 45 are directly applied to parameter estimator 70 via lines 81 and 82 and lines 93 and 94 (switches 91 and 92 are set so that tissue rejection filter 50 is bypassed). Parameter estimator 70 is a standard circuit used in typical modern ultrasonic color flow Doppler systems, such as the systems described in the above-referenced patent of Kim. As is well known, parameter estimator 70 estimates a complex autocorrelation signal for I and Q signals received from corner turning memory 45. Parameter estimator 70 outputs on lines 111, 112 and 113 estimates commonly referred to as P, D and N, respectively, which estimates are convertible using well known equations into three spectral moments representative of the input signal. The first spectral moment is representative of the power of the input signal and is proportional to the backscatter cross-section and the number of scatterers within a resolution volume. The second spectral moment is the mean frequency of the m input signal and is proportional to the mean radial velocity of scatterers within the resolution volume. The third spectral moment is representative of the spectral width or variance of the input signal which is caused by shear and/or turbulent motion of scatterers within the resolution volume. As is well known, each resolution volume has a multiplicity of I and Q samples, each sample resulting from one of the acoustic lines of the ensemble passing through the resolution volume at a particular beamline direction. For example, in a typical case there may be between 2 to 15 firings of probe 10 for each beamline, with between 50 to 1000 resolution volumes collected along a common beamline direction. Note, as is conventional, parameter estimator 70 also temporally averages the estimates developed at each range gate for every pair of acoustic lines so processed as to develop a single set of N, D, P estimates for each range gate in a given beamline direction.

The inventors have discovered that when forming the parameter estimation during the first read (or tissue motion estimation) operation, it is advantageous to utilize the data from less than all of the acoustic lines for each beamline direction. Less than all of the available data can be used for forming the tissue motion estimation, since: a) the tissue motion is generally slower than the blood motion, and therefore a lower PRF (pulse repetition frequency) can be used as compared with the PRF used for blood flow and still give accurate estimations without aliasing, and, b) the amplitude of the tissue motion signals is generally much greater than those developed by reflections from blood, thereby providing a relatively good S/N for the tissue motion signals. Thus, in accordance with a further embodiment of the present invention, the acoustic lines of the ensemble which are to be utilized should be evenly spaced throughout the ensemble, utilizing I and Q samples from every second acoustic line for each beamline (i.e., lines $i_0$, $i_2$ and $i_4$ of the six lines shown in FIG. 3b), or every fourth acoustic line and so forth.

FIG. 5 illustrates the effect of selectively skipping readout of data from corner turning memory 45 in this manner during the first read operation. As well known to those of ordinary skill in the art, for a given PRF, the maximum unambiguous detection of velocity corresponds to a frequency range between −PRF/2 and +PRF/2 (and velocities exceeding this range will be aliased). FIGS. 5a and 5b illustrate the tissue and flow portion of the spectral representation of the acoustic signals, wherein the plot of FIG. 5a is normalized with respect to frequency, and the plot of FIG. 5b is not normalized. Since tissue motion is generally not as fast as blood flow, during tissue motion estimation such a high PRF (and the correspondingly high signal processing speed) is not necessary. When, in accordance with this first aspect of the invention, i.e., every other acoustic line of data from the ensemble for each beamline is readout and used during the first read operation, the PRF (and maximum unambiguous velocity detection range) is cut in half, to ±PRF/4, as shown in FIG. 5b. This effectively "zooms-in" on the slower moving tissue signals, as shown in the normalized plot of FIG. 5c, and provides an accurate, unambiguous estimation of its velocity, while at the same time cutting in half the number of I/Q samples required to be processed, as compared to the amount of samples processed during estimation of blood flow. As one can readily appreciate from this, this embodiment of the present invention results in the utilization of appreciably less processing power, without the loss of useful tissue motion information, for accurately controlling a tissue motion rejection filter or some other controllable arrangement for tissue motion suppression (such as in the embodiment to be described in conjunction with FIG. 9). In fact, due to the above-described "zoom" effect, the potential for an even more accurate tissue parameter estimation is provided.

The output from parameter estimator 70 produced by the first read operation comprises estimates convertible into the three spectral moments for each of the resolution volumes for which estimates are computed, and this output is applied as input to tissue processor 90. In accordance with this embodiment of the invention, tissue processor 90 uses this output so as to adaptively and dynamically (continuously) develop Tissue Rejection Filter Control (TRFC) signals which are used to control filtering of the echo signals at each of the resolution volumes along each beamline direction upon their read-out from corner turning memory 45 during the second read operation, to thereby remove signal components representative of tissue motion. Thus, the TRFC signal is applied, via channel 114, as input to a tissue rejection filter 50. In this embodiment tissue rejection filter 50 is a programmable notch filter, for example, a programmable, complex notch filter (or, in an alternative embodiment, a pair of real notch filters, as will be described). In a preferred embodiment of this aspect of the present invention, the notch filter is a programmable complex digital filter whose coefficients are controlled dynamically and adaptively by TRFC signals on line 114. The TRFC signals transmitted over line 114 from tissue processor 90 can move: (a) the center of the notch—to a negative or positive frequency or leave it at the zero frequency—; (b) the shape of the notch; and/or (c) the width of the notch.

FIG. 6a shows an embodiment of a digitally programmable beamline filter 600 useful as a building block for constructing tissue rejection filter 50. As shown, input samples at point 602 proceed to filter output 604 by way of three different paths. The first path includes multiplier 606 and adders 608 and 610. A second path includes beamline delay 612, multiplier 614 and adders 608 and 610. A third path comprises beamline delays 612 and 616, multiplier 618 and adder 610. Each of delays 612 and 616 provides a time delay equal to a complete beamline, and provide storage for the total number of input samples in a beamline, and includes storage for the signal sample of a complete beamline. Control signals are applied to input 620, 622 and 624 of multipliers 606, 614 and 618, respectively, (as will be described in greater detail with respect to FIG. 8a) for setting the multiplying coefficient for multipliers 606, 614 and 618, respectively, which, in a manner well known to those of ordinary skill in the art, thereby programs beamline filter 600 to have a given width/shape of its attenuation versus frequency response characteristic.

FIG. 6b and FIG. 6c show examples of the selectable frequency response of filter 600 in response to two different sets of control signals. The control signals select multiplier coefficients, i.e., [0.25–0.5 0.25], to obtain the frequency response shown in FIG. 6b and the control signals select multiplier coefficients, i.e., [0.5–0.5 0.0], to obtain the frequency response shown in FIG. 6c.

Figure 7:
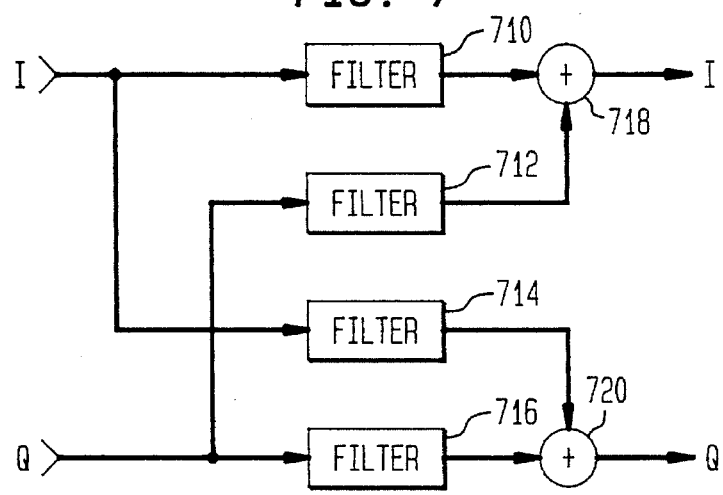

FIG. 7 shows the overall arrangement of a complex tissue rejection filter 50, using four of the programmable vector filters of the type shown in FIG. 6a. The I and Q signals are applied as inputs to filters 710, 714 and filters 712, 716, respectively. An adder 718 receives at its inputs the output from filters 710 and 712, and an adder 720 receives at its inputs the output from filters 714 and 716. The output of adder 718 is the filtered I signal and the output of adder 720 is the filtered Q signal. In this type of filter arrangement, filters 710 and 716 are commonly referred to as direct filters, while filters 714 and 712 are commonly referred to as cross filters. The TRFC signals are individually applied to filters 710, 712, 714 and 716 in the same manner as shown for filter 600 of FIG. 6a, for dynamically and adaptively developing a notch frequency response for tissue rejection filter 50 which continuously maximizes attenuation of the tissue signal components while minimizing attenuation of the blood flow signal components.

The development of TRFC signals will be described in greater detail later on with respect to FIG. 8, however, at this point it should be noted that in accordance with this aspect of one embodiment of the present invention, the estimate of tissue mean frequency is used to control the location of the center of the filter notch and the estimates of tissue power and spectrum width are used to control the notch shape and width. Clearly, however, other mapping formulas using fractional amounts of the power, frequency and width estimates, alone or in combination, could be used as well. As a result, tissue processor 90 develops TRFC signals which cause tissue rejection filter 50 to continuously maximize tissue (clutter) rejection while, at the same time, minimize attenuation of useful blood flow signals. For additional detail concerning variable coefficient filters used in clutter suppression, the reader is referred to Section 15.7 of the Skolnik reference, cited previously. Such filters can be designed to produce a wide variety of selectable filter profiles.

Before describing further details of tissue processor 90, the second read operation of corner turning memory 45, and a further aspect of an embodiment of the invention, will be described. For this operation, switches 91 and 92 are moved to a second position whereby tissue rejection filter 50 is not by-passed. Thus, during the second read operation, data read out of corner turning memory 45 are applied as input to tissue rejection filter 50 over lines 77 and 78. For each resolution volume, the characteristics of tissue rejection filter 50 are determined in response to the TRFC signals input over channel 114. Thus, in accordance with this embodiment of the invention, the filtered data output from tissue rejection filter 50 is applied as input to the same parameter estimator 70 as was used during the first read operation, over lines 87, 93 and 88, 94. In response, during the second read operation, parameter estimator 70 outputs estimates representative of the three spectral moments of the movement component of the I and Q signals which have been filtered by tissue rejection filter 50. These three estimates, now clutter canceled (e.g., moving tissue components are filtered out), are then applied as input to color scan converter 200 over lines 111, 112 and 113. It is noted that further processing of these signals may be performed by color flow processor 40 and that, for ease of understanding, such further processing is omitted from this description. By using the same corner turning memory and parameter estimator for tissue velocity estimation as is used for blood flow estimation, signal processing hardware complexity is reduced.

We now turn to a more detailed description of tissue processor 90 to describe development of the TRFC signals and two further aspects of an embodiment of the present invention. It is known that in the event that there happens to be no clutter, or very little clutter, conventional tissue motion rejection processing may actually remove some of the desired blood flow component. This, of course, is extremely undesirable because any attenuation or loss of the already very low-level blood flow signal will directly affect the quality of the reproduced blood flow image and/or data. The present inventors have observed that tissue motion signals quite often have statistical properties which are significantly different from those of blood flow, including larger spatial correlation, larger dynamic range, different spatial location, and so forth. In particular, they have observed that tissue motion signals generally have a large spatial correlation length compared with blood flow signals. The present inventors take advantage of this fact to provide effective tissue motion rejection while preventing inadvertent rejection of the blood flow component. Thus, in accordance with a further embodiment of the present invention, the tissue motion estimates are spatially averaged before being used to control tissue rejection filter 50.

As shown in FIG. 4, tissue processor 90 performs a spatial averaging by passing the NDP estimates representative of the three spectral moments through a spatial filter 116 (Note, as previously discussed with respect to the description of color flow processor 40, the beamline signal samples were also temporally averaged by the color flow processor). Spatial filter 116 essentially performs a smoothing function by averaging estimates from a given resolution volume with estimates from contiguously neighboring resolution volumes. This smoothing function may be understood more clearly by referring back to FIG. 3a. Data from resolution volume $V_{kl}$ is averaged axially with data from neighboring resolution volumes along beamline l, i.e. $V_{k-1,l}$, $V_{k+1,l}$, etc. and also laterally, by using data from beamlines neighboring beamline l, i.e. l–1 and l+1, at the same ranges, i.e., $V_{k-1,l-1}$; $V_{k,l-1}$; $V_{k+1,l-1}$; and $V_{k-1,l+1}$; $V_{k,l+1}$; $V_{k+1,l+1}$. It should be understood that this aspect of the present invention is not limited to averaging estimates of nearest neighbor resolution volumes, but may be extended to include other methods of selecting resolution volume estimates to be averaged. As one can readily appreciate from this, spatial filter 116 includes a beamline data memory (not specifically shown) for storing the necessary estimate data from neighboring resolution volumes to enable spatial filter 116 to carry out the above-described averaging process, and to also keep track of which averaged data should be used for controllably filtering the data for each resolution volume of each beamline supplied from corner turning memory 45 during the second read operation. It should also be appreciated that in an alternative embodiment, each average of the spectral estimates could be used for controllably filtering more than one of the resolution volumes (for example, those resolution volumes which were averaged together to form the averaged spectral estimate).

Furthermore, it is also noted that the spatial averaging algorithm used by spatial filter 116 could itself be adaptive. For example, as estimates are gathered for resolution volumes that are located deeper into the scanned area, the signal-to-noise ratio typically degrades. Therefore, a larger area of spatial averaging may be desired to prevent development of the TRFC signal to be affected by unwanted signal components. Thus, in a further alternative embodiment, the spatial averaging algorithm implemented by spatial filter 116 would change in response to changes in, e.g., the value of the power estimate component of the signals, so as to generally increase the spatial averaging provided as the echo signals come from locations deeper within the scanned area.

As was shown in FIG. 4, tissue processor 90 maps the spatially averaged NDP estimates output from spatial filter 116 over lines 118, 119, and 120, into the TRFC signals output over line 114, to control tissue rejection filter 50. This mapping is performed by a mapping processor 115 in conjunction with a signal output from a threshold comparator 117. In accordance with an embodiment of the present invention, it is desired to perform the mapping so as to adaptively select the characteristics of tissue rejection filter 50. Selection of the notch frequency and width of tissue rejection filter 50 depends first on properly identifying a tissue motion signal. In the illustrated embodiment, identification is accomplished by applying the estimate of the power signal on line 120 to the input of threshold comparator 117, where it is compared with a user-controlled threshold value applied as input on line 121. This threshold value is used with comparator 117 to identify as tissue motion estimates those estimates of the power spectral moment which have an amplitude (power) which exceeds the user set threshold. As a result, mapping processor 115 identifies the estimates as being associated with tissue motion whenever the estimate of power output over line 120 exceeds the user set threshold value. In such an instance, mapping processor 115 develops a TRFC signal which causes tissue rejection filter 50 to provide the characteristics of a desired notch filter. However, whenever the estimate of power falls below the threshold, mapping processor 115 generates a TRFC signal which causes tissue rejection filter 50 to perform minimal or no filtering of that resolution volume. In this regard, it should be clear that alternative embodiments are readily conceivable for identifying tissue motion, one such embodiment generally comprising, for example, providing threshold comparison for the N and D estimates, as well as the P estimate. In this case, additional threshold comparators 117 would be provided for the N and D estimates, respectively.

As previously noted, color flow processors 40 provides at its output signals known in the art as N, D and P. The P component is representative of the signal Power and the D and N components are convertible into estimations of the signal frequency (velocity, in the time domain) and variance (turbulence, in the time domain) in accordance with the following known equations:

$$\begin{aligned}
\text{Frequency} &= (1/2\pi)\arctan(N/D) \\
\text{Variance} &= 1 - R/P, \\
\text{where } R &= \sqrt{N^2 + D^2}
\end{aligned}$$

Figure 8A:
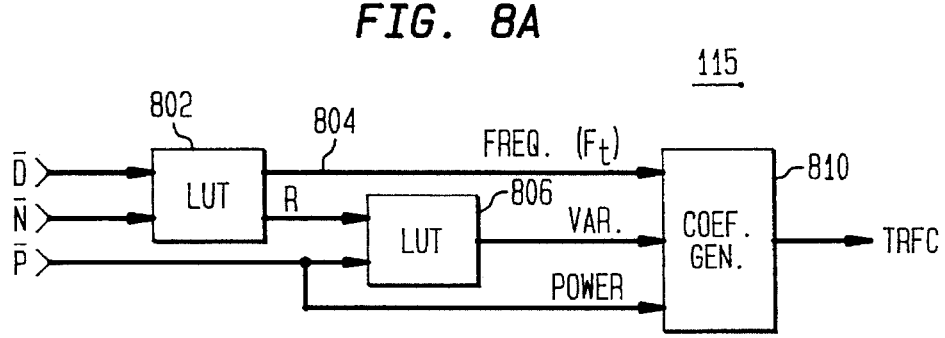
FIG. 8a shows details of a mapping processor used in the embodiment shown in FIG. 4, and FIGS. 8b and 8c illustrate examples of different notch filter characteristics which could be selected.
Figure 8B:
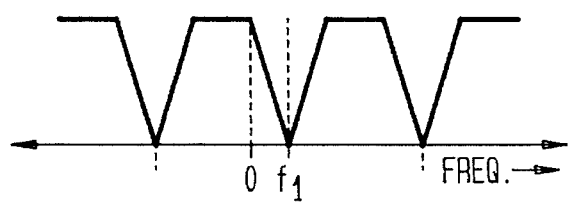
Figure 8C:
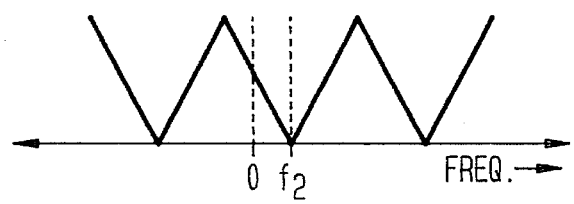

FIG. 8a shows details of one embodiment of mapping processor 115 of FIG. 4 which carries out the above-described conversion calculations. The averaged D and N components of the estimates provided from spatial filter 116 are applied as address inputs to a look-up table (LUT) 802. In response, LUT 802 outputs at line 804 a signal representative of the mean tissue frequency ($F_t$), which will be used for selecting the center frequency of the notch filter, and which, as previously noted, may also be used as a component in the mapping formulation for selecting the notch filter width. As well known, a LUT contains data at specifically addressed locations, which data is individually provided at the LUT output upon input of a specific address. As such, LUT are commonly used in a signal processing application to solve an equation when the value of all of the equation variables are known. Thus, LUT 802 contains a matrix of frequencies at its addressable locations which correspond to the calculation of Frequency using different values of N and D. Therefore, upon input of specific N and D averaged values as addresses to LUT 802, a corresponding Frequency is output on line 804. In a similar manner, the addressable locations of LUT 806 are loaded so as to cause LUT 806 to provide at its output the Variance value which corresponds to the values of the averaged Power and R variables which are provided as addresses to its input. The addressable locations of a final LUT 810 are loaded so as to cause LUT 810 to provide at its output the TRFC signals necessary for causing tissue rejection filter 50 to provided a desired frequency response, in response to the values of the Power, Frequency ($F_t$) and Variance components estimated for the tissue component of the Doppler signal, which were provided as addresses to its input. Basically, in the illustrated embodiment the value of the Frequency component determines the center frequency of the notch response of tissue rejection filter 50, and the Variance value, or the Variance in combination with the Power, determines the shape/width of the notch response. The precise matrix of tissue movement estimates versus TRFC signals is very application specific, and is left to the user to determine for a given application and then load the appropriate coefficients into LUT 810. FIG. 8b illustrates one example of a desired frequency response for tissue rejection filter 50, when the Power, Frequency and Variance components estimated for the tissue component of the Doppler signal indicate a velocity centered at $f_1$ and a relatively narrow spectral width. FIG. 8c illustrates a further example of a desired frequency response for tissue rejection filter 50 when the values of the Power, Frequency and Variance components estimated for the tissue component of the Doppler signal indicate a velocity centered at a somewhat lower frequency $f_2$ and having a relatively wider spectral width.

Figure 9:
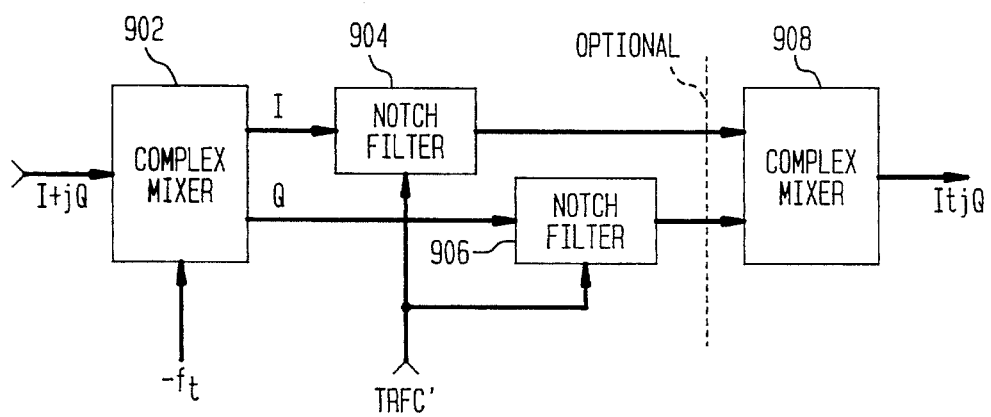
FIG. 9 illustrates an alternative embodiment for implementing a controlled notch filtering of the Doppler color flow signals, which uses real (as compared to complex) notch filters.

FIG. 9 illustrates an alternative embodiment for implementing the controlled notch filtering provided by tissue rejection filter 50, which uses a real (as compared to complex) filter arrangement. In this embodiment, the baseband quadrature I and Q beamline output signals provided from corner turning memory 45 are applied as one input to a complex mixer 902. A second input to mixer 902 could be a complex sinusoid (i.e., $I_t-jQ_t$) generated by a complex signal oscillator which is responsive to the negative frequency estimate component of the tissue movement signal, $-F_t$ (developed in a similar manner to the development of $F_t$ as shown in FIG. 8a). In response, as well known, mixer 902 downconverts the frequency spectrum of the input signals so that the tissue movement component is translated to a relative frequency of zero. Thereafter, the quadrature I and Q outputs of mixer 902 are separately notched filtered by real notch filters 904 and 906, respectively, both of which are dynamically and adaptively controlled by TRFC signals which are developed in a manner similar to the development of the TRFC signals shown in FIG. 8a. In a manner similar to the control of filters 710–716 of FIG. 7, TRFC signals control filters 904 and 906 so that their notch shape and width correspond to a desired shape and width which will maximize attenuation of the unwanted tissue movement signals and minimize attenuation of the desired blood flow signal. Optionally, in applications where absolute velocity accuracy is important, after filters 904,906, an additional stage of complex mixing can be provided. Thus, a mixer 908 would receive at one input the notch filtered I and Q baseband signals, and its other input using $+f_t$ for generating a complex sinusoid $I_t+jQ_t$) which is applied as a mixing signal, so as to upconvert the frequency components of the notch filtered I and Q signals, thereby translating them back to their original baseband positions.

Figure 10:
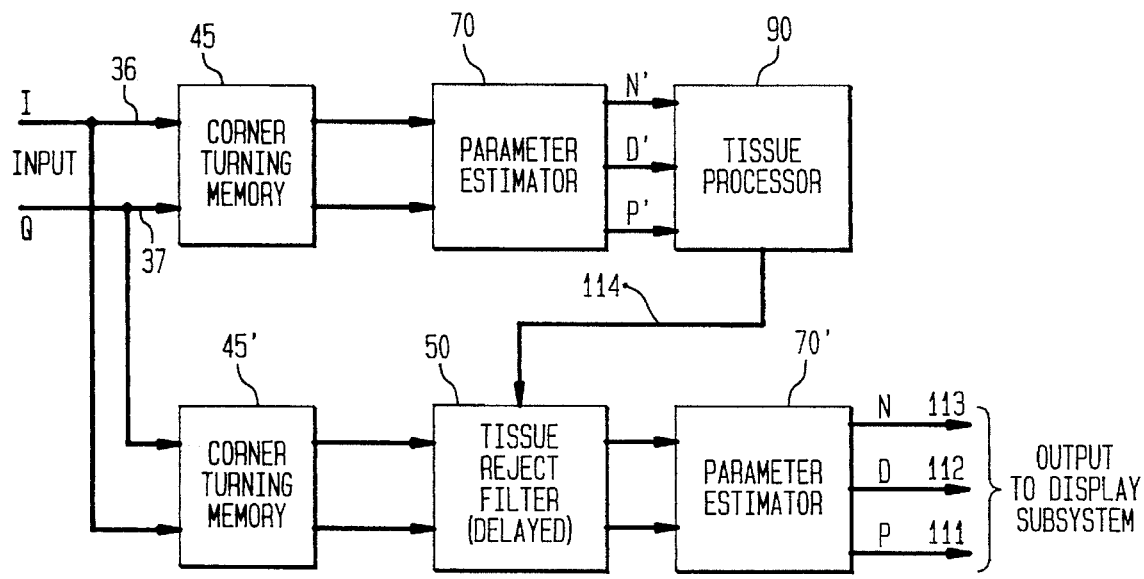
FIG. 10 illustrates an alternative embodiment of the color flow processor shown in FIG. 4.

FIG. 10 illustrates a further embodiment of the present invention as an alternative embodiment of the colorflow processor 40 of FIG. 4. Recall that in the embodiment shown in FIG. 4, color flow processor 40 was operating in a time sequential mode, first to provide estimates used for developing the TRFC signals, and then to provide estimates of the clutter cancelled color flow signals. The FIG. 10 embodiment eliminates the need for switches 91,92 shown in FIG. 4, and instead an additional corner turning memory and parameter estimator is provided so that the tissue signal processing can be carried out substantially simultaneously in a separate path. Although an additional corner turning memory and a second parameter estimator are required in this embodiment, this arrangement is particularly advantageous when it is desired to maintain a relatively high frame rate for providing the blood flow image to a display, in spite of significant signal processing to be performed on the Doppler signals.

As shown in FIG. 10 input signals I and Q on lines 36, 37 are stored in corner turning memory 45 as well as in a corner turning memory 45'. Output from memory 45 is transmitted to parameter estimator 70 in the manner described previously, and the resulting tissue signal estimates, denoted as N', D' and P', are sent to tissue processor 90, which generates the previously described TRFC signals on line 114. In response to the TRFC signals, tissue rejection filter 50 removes the tissue movement signal component, as previously described. The resulting signal is then processed by an additional parameter estimator 70' to produce the output signals P, D, and N on lines 111,112, and 113 respectively. In this configuration the tissue rejection filter must be modified to provide a time delay in order to compensate for the tissue signal processing time in parameter estimator 70 and tissue processor 90.

Additionally, it is noted that the aspect of the invention illustrated by FIG. 10 is not limited to the precise configuration described. While the described example used physically separate corner turning memories 45,45', the function of these two memories could be performed by suitable control of a single memory device.

Figure 11:
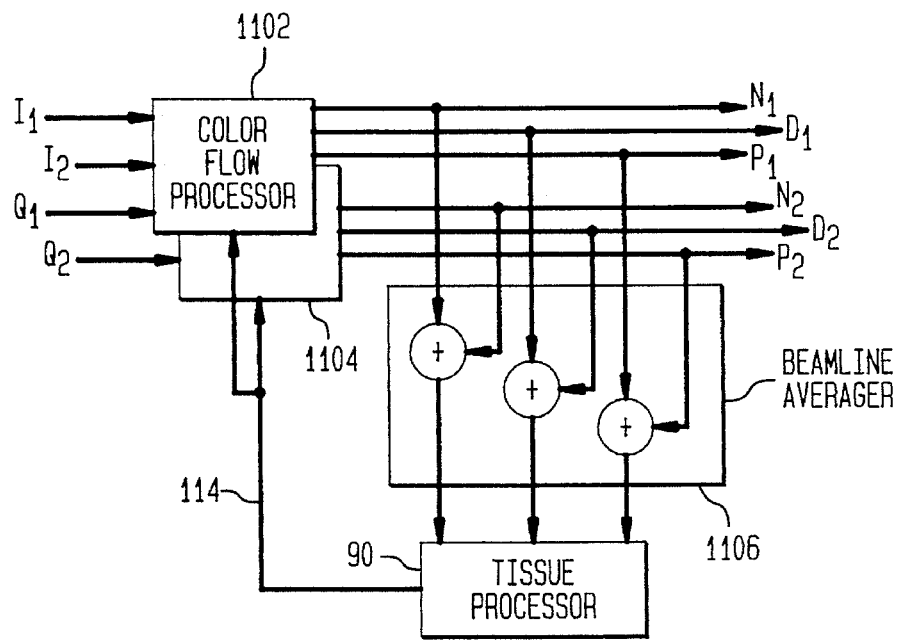
FIG. 11 illustrates a further embodiment of the present invention which has a plurality of parallel beamforming channels for developing multiple colorflow beamlines substantially simultaneously with one another.

In this regard, FIG. 11 illustrates a further alternative embodiment of the present invention useful in an diagnostic ultrasound imager having a plurality of parallel beamforming channels for developing parallel beams substantially simultaneously with one another. Here, a separate set of I and Q signals are provided for each one of the parallel beamforming channels. For the sake of simplicity only two parallel beamforming channels are shown, while four, or even more of such channels may be used. Techniques for developing such parallel beams are well known to those of ordinary skill in the art, and basically comprise applying different sets of beamforming/focussing delays to the received echoes, each set of delays developing a different set of scanning beamlines, 1,2, etc. One embodiment useful for the present application is shown, for example in U.S. patent application Ser. No. 08/270,868 entitled Multi-Beam Digital Beamforming Method and Apparatus, filed on Jul. 5, 1994, invented by Kim et al.

As shown in FIG. 11, first and second sets of signals (i.e., $I_1,Q_1$, and $I_2,Q_2$) from first and second beamformers (not specifically shown) are applied to color flow processors 1102 and 1104, respectively. The construction and operation of color flow processors 1102 and 1104 is substantially the same as color flow processor 40 shown and described with respect to FIG. 4. The N,D and P output signals from processor 1102 are averaged with the respective N,D and P output signals from processor 1104 (i.e., those at the same range gate of an adjacent beamline), via beamline averager 1106. Beamline averager 1106 basically comprises an individual signal combiner/decimator for each pair of the N, D and P estimates provided by the color flow processors 1102,1104, for developing, in a manner well known to those of ordinary skill in the digital signal processing art, an average of the digital signals applied to their inputs. The averaged values, N, D and P are then applied as input to tissue processor 90 for development of the TRFC signals in the same manner as the development of the TRFC signals shown and described in conjunction with FIG. 8a. The TRFC signals are then applied to dynamically and adaptively control the tissue rejection filters 50 located in each of color flow processors 1102 and 1104, in a manner as previously described in conjunction with FIGS. 4–8.

Figure 12:
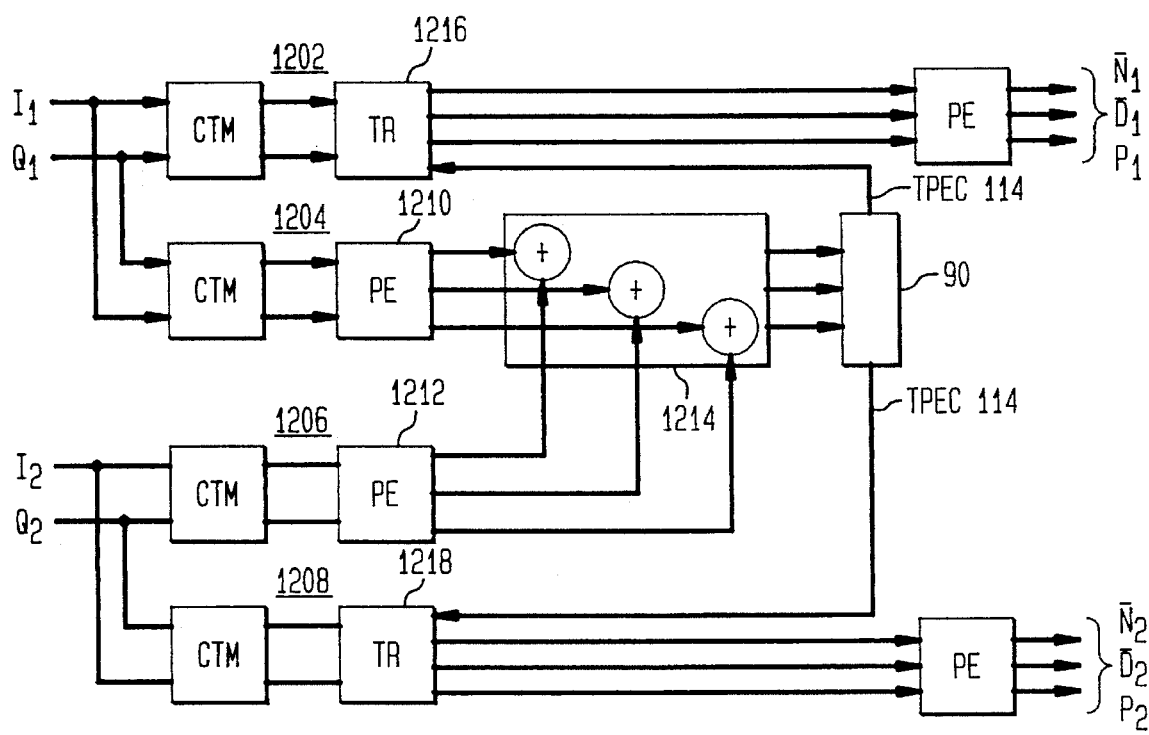
FIG. 12 illustrates an even further embodiment of the invention, where the alternative technique shown in FIG. 10 is used in a parallel beamforming ultrasound imager of the type shown in FIG. 11.

FIG. 12 illustrates an even further alternative embodiment of the invention, wherein the technique of FIG. 10 is used in a parallel beamforming ultrasound imager, e.g., of the type shown in FIG. 11. Again, only two parallel beamforming channels 1 and 2 are shown, however, as described above with respect to FIG. 11, four or even more can be provided. As shown, two signal processing paths, 1202,1204 and 1206,1208 are provided for each of the beamforming channels 1 and 2, respectively. Each path includes its own corner turning memory and parameter estimator. Estimates of the tissue motion for each of the beams is developed by parameter estimators 1210 and 1212 and provided to a beamline averager 1214 which averages the estimates in the same manner provided by beamline averager 1106 of FIG. 11. Beamline averager 1214 then provides a single set of parameter estimates to tissue processors 90 which, as described in the previous embodiments, generates a TRFC signal which is applied via lines 114 to tissue rejection filters 1216,1218 for operating the rejection filters so as to removing the tissue motion clutter signal components from the blood flow image signal in same manner as previously described.

I claim:

1. An ultrasonic flow imaging and/or measuring system comprising:

a transmitter/receiver arrangement for transmitting a plurality of ultrasonic pulses into an area to be scanned and developing a corresponding plurality of acoustic line signals for each beamline of the scanned area in response to processing of reflections of said transmitted ultrasonic pulses received from within said scanned area;

a memory, operative during a write mode for receiving and storing said acoustic line signals as a plurality of sequential samples for each acoustic line, and operative during a read-out mode for supplying said samples of said acoustic lines at a memory output;

a tissue motion rejection arrangement having a signal input responsive to said acoustic line samples from said memory output, and a control input responsive to a control signal representative of tissue movement within said scanned area, said tissue motion rejection arrangement being responsive to said control signal for processing said acoustic line signals so as to provide at an output filtered acoustic line signals wherein signal components representative of tissue movement within said scanned area are suppressed;

a flow processor responsive to said acoustic line signals for developing therefrom estimate signals representative of movement in said scanned area; and, a signal directing means, operative in a first mode for applying said acoustic line signals from said memory output to said flow processor without any intervening processing, and operative in a second mode for applying said acoustic line signals to said flow processor via said tissue motion rejection arrangement.

2. The ultrasonic flow imaging and/or measuring system of claim 1, wherein said signal directing means comprises a switch means having first and second inputs and a common output, said first and second inputs being responsive to said memory output and said filter output, respectively, and said common output is coupled to an input of said flow processor.

3. The ultrasonic flow imaging and/or measuring system of claim 1, wherein said tissue motion rejection arrangement comprises a controllable notch filter.

4. The ultrasonic flow imaging and/or measuring system of claim 3, wherein said controllable notch filter comprises a controllable complex notch filter.

5. The ultrasonic flow imaging and/or measuring system of claim 1, wherein said tissue motion rejection arrangement comprises a controllable complex mixer providing quadrature output signals, for frequency translating the tissue motion component of said beamline signals to a given reference frequency, and an arrangement of real filters responsive to said output signals of said complex mixer for suppressing said tissue movement component from said beamline signals.

6. The ultrasonic flow imaging and/or measuring system of claim 1, further including a tissue processor coupled to said flow processor and responsive to said estimate signals provided therefrom during said first mode of operation for adaptively and dynamically generating said control signal.

7. The ultrasonic flow imaging and/or measuring system of claim 6, wherein said flow processor provides estimates representative of spectral moments of said acoustic line signals, and said tissue processor includes means for determining which of said spectral estimates are representative of movement in non-flow portions of said scanned area in order to develop said control signal using said estimates so identified.

8. The ultrasonic flow imaging and/or measuring system of claim 7, wherein said tissue processor includes means for determining a unique value for said control signal in response to said spectral estimates provided by the parameter estimator and identified as being representative of non-flow portions of said scanned area.

9. The ultrasonic flow imaging and/or measuring system of claim 8, wherein said means for determining includes at least one look-up table having address inputs responsive to one or more of said spectral estimates and an output for providing said tissue rejection filter control signal.

10. The ultrasonic flow imaging and/or measuring system of claim 6, wherein said flow processor comprises an autocorrelator whose outputs are directly applied to said tissue processor, without conversion to velocity estimate signals, for generation of said control signal.

11. A method for ultrasonic flow imaging and/or measuring system comprising the following steps:

transmitting a plurality of ultrasonic pulses into an area to be scanned and developing a corresponding plurality of acoustic line signals for each beamline of the scanned area in response to processing of reflections of said transmitted ultrasonic pulses received from within said scanned area;

operating a memory during a write mode for receiving and storing said acoustic line signals as a plurality of sequential samples for each acoustic line, and operating a memory during a read-out mode for supplying said samples of said acoustic lines at a memory output;

filtering said acoustic line signals in a tissue motion rejection arrangement having a signal input responsive to said acoustic line samples from said memory output, and a control input responsive to a control signal representative of tissue movement within said scanned area, so as to provide at an output filtered acoustic line signals wherein signal components representative of tissue movement within said scanned area are suppressed;

flow processing said acoustic line signals for developing therefrom estimate signals representative of movement in said scanned area; and, directing, during a first time period, said acoustic line signals from said memory output to said flow processor without any intervening filtering for suppression of signal components representative of tissue movement within said scanned area, and directing, during a second time period, said acoustic line signals from said memory output to said flow processor with intervening filtering by said tissue motion rejection arrangement for suppression of signal components representative of tissue movement within said scanned area.

12. The method of claim 11, wherein said directing step comprises selective operation of a switch having first and second inputs and a common output, said first and second inputs receiving said acoustic line signals from said memory output and said filter output, respectively, and said common output providing said acoustic line signals to an input of said flow processor.

13. The method of claim 11, wherein said filtering step comprises controllable complex notch filtering.

14. The method of claim 11, wherein said filtering step comprises controllable complex mixing of the tissue motion component of said beamline signals for frequency translating them to a given reference frequency, and notch filtering with an arrangement of real filters responsive to said output signals of said complex mixer for suppressing said tissue movement component from said beamline signals.

15. An ultrasonic flow imaging and/or measuring system comprising:

a transmitter/receiver arrangement for transmitting a plurality of ultrasonic pulses into an area to be scanned and developing a corresponding plurality of acoustic line signals for each beamline of the scanned area in response to processing of reflections of said transmitted ultrasonic pulses received from within said scanned area;

a memory, operative during a write mode for receiving and storing said acoustic line signals as a plurality of sequential samples for each acoustic line, and operative during a read-out mode for supplying said samples of said acoustic lines at a memory output;

a flow processor responsive to said acoustic line signals for developing therefrom estimate signals representative of movement in said scanned area; and a signal processing path including a tissue motion filter arrangement, operative in a first mode for applying said acoustic line signals from said memory output to said flow processor without suppression of acoustic line signal components representative of tissue movement, and operative in a second mode for applying said acoustic line signals from said memory output to said flow processor with suppression of acoustic line signal components representative of tissue motion; and display means, responsive to said estimate signals developed by said flow processor during said second mode of operation of said signal processing path, for generating a display of an ultrasonic flow image and/or measurement.

16. The ultrasonic flow imaging and/or measuring system of claim 15, wherein said tissue motion filter arrangement has a signal input responsive to said acoustic line samples from said memory output, and a control input responsive to a control signal representative of tissue movement within said scanned area, said tissue motion filter arrangement being responsive to said control signal during said second mode for processing said acoustic line signals so as to provide at an output filtered acoustic line signals wherein signal components representative of tissue movement within said scanned area are suppressed.

17. The ultrasonic flow imaging and/or measuring system of claim 16, further including:

a tissue processor coupled to said flow processor and responsive to said estimate signals developed by said flow processor during said first mode of operation, for adaptively and dynamically generating said control signal.

* * * * *